United States Patent [19]

Baumgarth et al.

[11] Patent Number: 5,132,307
[45] Date of Patent: Jul. 21, 1992

[54] TETRALIN COMPOUNDS

[75] Inventors: Manfred Baumgarth, Darmstadt; Rolf Gericke, Seeheim; Rolf Bergmann, Reichelsheim; Jacques De Peyer, Pfungstadt; Ingeborg Lues, Darmstadt, all of Fed. Rep. of Germany

[73] Assignee: Merck Patent Gesellschaft Mit Beschrankter Haftung, Darmstadt, Fed. Rep. of Germany

[21] Appl. No.: 432,836

[22] Filed: Nov. 7, 1989

[30] Foreign Application Priority Data

Nov. 8, 1988 [DE] Fed. Rep. of Germany ....... 3837809

[51] Int. Cl.$^5$ .......................................... C07D 237/14
[52] U.S. Cl. .................... 514/247; 514/255; 514/256; 514/269; 514/272; 514/345; 514/347; 514/351; 514/352; 514/357; 514/408; 514/424; 514/426; 544/224; 544/230; 544/239; 544/240; 544/242; 544/298; 544/335; 544/336; 544/408; 546/195; 546/290; 548/543; 548/564
[58] Field of Search ............... 514/345, 347, 317, 319, 514/247, 351; 546/290, 195; 544/224, 230, 239, 240

[56] References Cited

U.S. PATENT DOCUMENTS

| | | | |
|---|---|---|---|
| 2,707,470 | 12/1972 | Sawa et al. | 546/15 |
| 3,707,474 | 12/1972 | Razdan | 546/269 |
| 3,853,899 | 12/1974 | Fake | 546/269 |
| 3,947,462 | 3/1976 | Arendson | 546/290 |
| 4,408,057 | 10/1983 | Engel | 544/224 |
| 4,446,113 | 5/1984 | Evans et al. | |
| 4,486,428 | 12/1984 | Eggler et al. | 514/253 |
| 4,542,149 | 9/1985 | Evans et al. | 514/422 |
| 4,634,705 | 1/1987 | DeBernardis et al. | 514/256 |
| 4,640,928 | 2/1987 | Willcocks | 514/422 |
| 4,644,070 | 2/1987 | Evans et al. | 549/399 |
| 4,772,603 | 9/1988 | Evans | 514/241 |
| 4,782,083 | 11/1988 | Cassidy et al. | 514/337 |
| 4,786,639 | 11/1988 | Evans | 514/254 |
| 4,800,212 | 1/1989 | Evans et al. | 514/424 |
| 4,882,352 | 11/1989 | Horn | 514/319 |
| 4,931,457 | 6/1990 | Effland et al. | 514/349 |
| 4,999,371 | 3/1991 | Englert et al. | 514/337 |
| 5,043,344 | 8/1991 | Englert et al. | 514/337 |
| 5,053,430 | 10/1991 | Gravery et al. | 514/337 |
| 5,071,871 | 10/1991 | Blarer et al. | 514/258 |

FOREIGN PATENT DOCUMENTS

| | | |
|---|---|---|
| 0204285 | 12/1986 | European Pat. Off. . |
| 0273262 | 10/1987 | European Pat. Off. . |
| 0296975 | 12/1988 | European Pat. Off. . |
| 0400430 | 12/1990 | European Pat. Off. ............ 544/238 |
| 89/10925 | 11/1989 | PCT Int'l Appl. . |

OTHER PUBLICATIONS

Ueda et al., Chem Abstr vol. 106, No. 17 Entry 138443 (1987) abstracting EP 204 285.
Buckle et al., Chem. Abstr. vol. 113 entry 6311a (1990) abstracting WO 89-10,925.

Primary Examiner—Donald G. Daus
Attorney, Agent, or Firm—Millen, White & Zelano

[57] ABSTRACT

New tetralin derivatives of the formula I

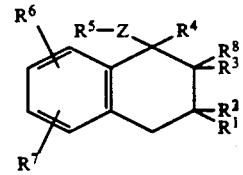

wherein $R^1$ to $R^8$ and Z have the meanings indicated herein and salts thereof, exhibit an effect on the cardiovascular system.

14 Claims, No Drawings

TETRALIN COMPOUNDS

SUMMARY OF THE INVENTION

The invention relates to tetralin derivatives of the formula I

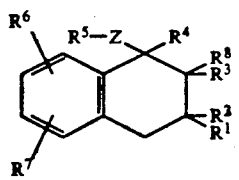

wherein
$R^1$, $R^2$ and $R^8$ are each H or A, $R^1$ and $R^2$ together can also be alkylene having 3-6 C atoms, $R^3$ is H, OH, OA or OAc, $R^4$ is H, $R^3$ and $R^4$ together can also be a bond, $R^5$ is a pyridyl, pyridazinyl, pyrimidinyl, pyrazinyl, oxodihydropyridyl, oxodihydropyridazinyl, oxodihydropyrimidinyl, oxodihydropyrazinyl or oxodihydropyrrolyl radical which is unsubstituted or is monosubstituted or disubstituted by A, F, Cl, Br, I, OH, OA, OAc, SH, NO₂, NH₂, AcNH, HOOC and/or AOOC, $R^6$ and $R^7$ are each H, A, HO, AO, CHO, ACO, ACS, HOOC, AOOC, AO—CS, ACOO, A—CS—O, hydroxyalkyl having 1-6 C atoms, mercaptoalkyl having 1-6 C atoms, NO₂, NH₂, NHA, NA₂, CN, F, Cl, Br, I, CF₃, ASO, ASO₂, AO—SO, AO—SO₂, AcNH, AO—CO—NH, H₂NSO, HANSO, A₂NSO, H₂NSO₂, HANSO₂, A₂NSO₂, H₂NCO, HANCO, A₂NCO, H₂NCS, HANCS, A₂NCS, ASONH, ASO₂NH, AOSONH, AO-SO₂NH, ACO—alkyl, nitro-alkyl, cyano-alkyl, A—C(=NOH) or A—C (=NNH₂), Z is O, S, NH or a bond, A is alkyl having 1-6 C atoms.
-alkyl is alkylene having 1-6 C atoms and Ac is alkanoyl having 1-8 atoms or aroyl having 7-11 C atoms, and salts thereof.

In the foregoing, selection of variables defined together is made independently.

Similar compounds are disclosed in EP-A 168,619.

An object of the invention is to provide new compounds which have valuable properties, particularly those which can be used for the preparation of medicaments.

It has been found that the compounds of the formula I and their physiologically acceptable salts possess valuable pharmacological properties and are well tolerated. Thus, they exhibit an action on the cardiovascular system in which, as a rule, a selective attack on the coronary system can be observed at fairly low doses and a hypotensive effect can be observed at fairly high doses. On the coronary system, for example, lowering of resistance and increase of flow take place, and the effect on the heart rate remains low. Furthermore, the compounds exhibit a relaxing action on various smooth muscular organs (gastro-intestinal tract, respiratory system and uterus). The action of the compounds can be determined by means of methods known per se such as are indicated, for example, in EP-A-76,075 (U.S. Pat. Nos. 4,446,113; 4,542,149; 4,640,928; and 4,644,070), EP-A-168,619 (U.S. Pat. No. 4,800,212), EP-A-173,848 (U.S. Pat. No. 4,772,603) or AU-A-45,547/85 (U.S. Pat. No. 4,786,639) (Derwent Farmdoc No. 86,081,769) and also by K. S. Meesmann et al., Arsneimittelforschung 25 (11), 1975, 1770-1776. Examples of suitable test animals are mice, rats, guinea pigs, dogs, cats, monkeys or pigs.

The compounds can therefore be used as active compounds for medicaments in human and veterinary medicine. They can also be used as intermediate products for the preparation of further active compounds for medicaments.

In the formulae indicated A is an alkyl group, preferably unbranched, having 1-6, preferably 1-4 and especially 1, 2 or 3, C atoms, specifically preferably methyl and also preferably ethyl, propyl, isopropyl, butyl or isobutyl and also preferably sec.-butyl, tert.-butyl, pentyl, isopentyl (3-methylbutyl), hexyl or isohexyl (4-methylpentyl).

If $R^1$ and $R^2$ together are alkylene, the alkylene group is preferably unbranched and is, specifically preferably —(CH₂)ₙ—, n being 3, 4, 5 or 6.

The group "-alkyl" is preferably —CH₂— or —CH₂CH₂—.

Ac is preferably alkanoyl having 1-6, in particular 1, 2, 3 or 4, C atoms, specifically preferably formyl or acetyl, and also preferably propionyl, butyryl, isobutyryl, pentanoyl or hexanoyl, and also preferably benzyol, o-, m- or p-toluyl, 1-naphthoyl or 2-naphthoyl.

$R^1$ and $R^2$ are preferably each alkyl, in particular each methyl or ethyl, and preferably each methyl.

$R^3$ and $R^4$ are preferably together a bond. If $R^4$ is H, $R^3$ is preferably OH, O-CHO or O-COCH₃.

If Z is a bond, $R^5$ is preferably unsubstituted 2-oxo-1,2-dihydro-1-pyridyl(1H-2-pyridon-1-yl), 3-hydroxy-6-oxo-1,6-dihydropyridazin-1-yl or 2-oxo-4-hydroxy-1,2-dihydro-1-pyridyl, and also preferably unsubstituted 2-oxo-1,2-dihydropyrazin-1-yl, 6-oxo-1,6-dihydropyridazin-1-yl, 2-oxo-1,2-dihydropyrimidin-1-yl, 6-oxo-1,6-dihydropyrimidin-1-yl, 2-oxo-2,3-dihydropyrrol-1-yl, 2-oxo-2,5-dihydropyrrol-1-yl or 2-thioxo-1,2-dihydropyridin-1-yl. If $R^5$ is a substituted pyridone or thiopyridone ring, this ring is preferably monosubstituted in the 3-, 4- or 5-position or is disubstituted in the 3-position and the 5-position. Particularly preferred substituents are OH, NO₂ and NH₂, and also AOOC, OA, Cl, Br and NHCOCH₃; particularly preferred substituted radicals $R^5$ are specifically 4-, 3-, 5- and 6-hydroxy-2-oxo-1,2-dihydro-1-pyridyl or 4-, 3-, 5- and 6-hydroxy-2-thioxo-1,2-dihydro-1-pyridyl, 3-, 4-, 5- or 6-methoxy-1-oxo-1,2-dihydro-1-pyridyl or 3-, 4-, 5- or 6-methoxy-2-thioxo-1,2-dihydro-1-pyridyl, 3-, 4-, 5- or 6-acetoxy-2-oxo-1,2-dihydro-1-pyridyl or 3-, 4-, 5- or 6-acetoxy-2-thioxo-1,2-dihydro-1-pyridyl, 3-, 5- or 6-chloro-2-oxo-1,2-dihydro-1-pyridyl or 3-, 5-or 6-chloro-2-thioxo-1,2-dihydro-1-pyridyl, 3-nitro- or 5-nitro-2-oxo-1,2-dihydro-1-pyridyl or 3-nitro-or 5-nitro-2-thioxo-1,2-dihydro-1-pyridyl, 3-amino- or 5-amino-2-oxo-1,2-dihydro-1-pyridyl or 3-amino- or 5-amino-2-thioxo-1,2-dihydro-1-pyridyl, 3-carboxy- or 5-carboxy-2-oxo-1,2-dihydro-1-pyridyl or 3-carboxy- or 5-carboxy-2-thioxo-1,2-dihydro-1-pyridyl, 3-methoxycarbonyl- or 5-methoxycarbonyl-2-oxo-1,2-dihydro-1-pyridyl or 3-methoxycarbonyl-or 5-methoxycarbonyl-2-thioxo-1,2-dihydro-1-pyridyl, 3-ethoxycarbonyl- or 5-ethoxycarbonyl-2-oxo-1,2-dihydro-1-pyridyl or 3-ethoxycarbonyl- or 5-ethoxycarbonyl- 2-thioxo-1,2-dihydro-1-pyridyl, 3-acetamido- or 5-acetamido-2-oxo-1,2-dihydro-1-pyridyl or 3-acetamido- or 5-acetamido-2-thioxo-1,2-dihydro-1-pyridyl, 3,5-dichloro-, 3,5-dibromo-, 3-chloro-5-nitro-, 3-nitro-5-chloro-, 3-bromo-5-nitro-, 3-nitro-5-bromo, 3,5-dinitro-, 3-chloro-5-amino-, 3-amino-5-chloro-, 3-bromo-5-amino-, 3-amino-5-bromo-, 3- chloro-5-acetamido-, 3-acetamido-5-chloro, 3-bromo-5-acetamido- and 3-acetamido-5-bromo-2-oxo-1,2-dihydro-1-pyridyl or 3,5-dichloro-, 3,5-dibromo-, 3-chloro-5-nitro-, 3-nitro-5-chloro-, 3-bromo-5-nitro-, 3-nitro-5-bromo-, 3,5-dinitro-, 3-chloro-5-amino-, 3-amino-5-chloro-, 3-bromo-5-amino-, 3-amino-5-bromo-, 3-chloro-5-acetamido-, 3-acetamido-5-chloro-, 3-bromo-5-acetamido and 3-acetamido-5-bromo-2-thioxo-1,2-dihydro-1-pyridyl, 4-hydroxy-6-oxo-1,6-dihydropyridazin-1-yl, 5-hydroxy-6-oxo-1,6-dihydropyridazin-1-yl, 3-, 4- or 5-methoxy-6-oxo-1,6-dihydropyridazin-1-yl, 3-, 4- or 5-ethoxycarbonyl-6-oxo-1,6-dihydropyrimidin-1-yl, 2-hydroxy-6-oxo-1,6-dihydropyrimidin-1-yl or 4-hydroxy-6-oxo-1,6-dihydropyrimidin-1-yl.

If Z is O, S or NH, $R^5$ is preferably 6-hydroxy-3-pyridazinyl (=1,6-dihydro-6-oxo-3-pyridazinyl) or 2-hydroxy-4-pyridyl (=1,2-dihydro-2-oxo-4-pyridyl), and also preferably unsubstituted 2-, 3- or 4-pyridyl, 2-, 4-or 5-pyrimidinyl, 3-, 4- or 5-pyridazinyl, 3-, 4- or 5-pyrazinyl, hydroxypyridyl, such as 3-, 4-, 5- or 6-hydroxy-2-pyridyl, 2-, 4- or 5-hydroxy-3-pyridyl, 3-hydroxy-4-pyridyl or 2-hydroxy-5-pyridyl; hydroxypyridazinyl, such as 4-hydroxy-3-pyridazinyl, 5-hydroxy-3-pyridazinyl or 3-, 5- or 6-hydroxy-4-pyridazinyl; hydroxypyrimidinyl, such as 4-hydroxy-2-pyrimidinyl, 5-hydroxy-2-pyrimidinyl, 2-, 5- or 6-hydroxy-4-pyrimidinyl, 2-hydroxy-5-pyrimidinyl or 4-hydroxy-5-pyrimidinyl; hydroxypyrazinyl, such as 3-, 5- or 6-hydroxy-2-pyrazinyl; dihydroalkyloxopyridyl, such as 1,2-dihydro-1-methyl-2-oxo-3-, -4o-, -5- or -6- pyridyl, 1,2-dihydro-1-ethyl-2-oxo-3-, -4-, -5- or -6-pyridyl; dihydroalkyloxopyridazinyl, such as 1,6-dihydro-1-methyl-6-oxo-3-, -4- or -5-pyridazinyl or 1,6-dihydro-1-ethyl-6-oxo-3-, -4- or -5-pyridazinyl; alkoxypyridyl, such as 3-, 4-, 5- or 6-methoxy-2-pyridyl, 2-, 4- or 5-methoxy-3-pyridyl, 2-methoxy-4-pyridyl, 3-methoxy-4-pyridyl, 2-methoxy-5-pyridyl, 2-ethoxy-4-pyridyl or 3-ethoxy-4-pyridyl; alkoxypyridazinyl, such as 4-, 5- or 6-methoxy-3-pyridazinyl, 4-, 5- or 6-ethoxypyridazinyl, 3-, 5- or 6-methoxy-4-pyridazinyl or 3-, 5- or 6-ethoxy-4-pyridazinyl; alkoxypyrimidinyl, such as 4-methoxy-2-pyrimidinyl, 5-methoxy-2-pyrimidinyl, 2-, 5- or 6-methoxy-4-pyrimidinyl, 2-methoxy-5-pyrimidinyl or 4-methoxy-5-pyrimidinyl; alkoxypyrazinyl, such as 3-, 5- or 6-methoxy-2-pyrazinyl; aminopyridyl, such as 3-, 4-, 5-or 6-aminopyridyl, 2-, 4- or 5-amino-3-pyridyl, 2-amino-4-pyridyl, 3-amino-4-pyridyl or 2-amino-5-pyridyl; aminopyridazinyl, such as 4-, 5- or 6-aminopyridazinyl or 3-, 5- or 6-amino-4-pyridazinyl; aminopyrimidinyl, such as 4-amino-2-pyrimidinyl, 5-amino-2-pyrimidinyl, 2-, 5- or 6-amino-4-pyrimidinyl, 2-amino-5-pyrimidinyl or 4-amino-5-pyrimidinyl; aminopyrazinyl, such as 3-, 5- or 6-amino-2-pyrazinyl; mercaptopyridyl, such as 3-, 4-, 5- or 6-mercapto-2-pyridyl, 2-, 4- or 5-mercapto-3-pyridyl, 2-mercapto-4-pyridyl (=1,2-dihydro-2-thioxo-4-pyridyl), 3-mercapto-4-pyridyl or 2-mercapto-5-pyridyl; mercaptopyridazinyl, such as 4-, 5- or 6-mercapto-3-pyridazinyl (=1,6-dihydro-6-thioxo-3-pyridazinyl) or 3-, 5- or 6-mercapto-4-pyridazinyl; mercaptopyrimidinyl, such as 4-mercapto-2-pyrimidinyl, 5-mercapto-2-pyrimidinyl, 2-, 5- or 6-mercapto-4-pyrimidinyl, 2-mercapto-5-pyrimidinyl or 4-mercapto-5-pyrimidinyl; or mercaptopyrazinyl, such as 3-, 5- or 6-mercapto-2-pyrazinyl.

Those radicals $R^5$ which contain a hydroxyl or mercapto group adjacent to a ring N atom can also exist in the tautomeric lactam or thiolactam form, as indicated above in individual cases.

In $R^6$ and $R^7$ the symbols preferably are as follows:
A: methyl, and also ethyl; AO: methoxy, and also ethoxy; ACO: acetyl, and also propionyl; ACS: thioacetyl, and also thiopropionyl; AOOC: methoxycarbonyl, and also ethoxycarbonyl; AO—CS: methoxythiocarbonyl, and also ethoxythiocarbonyl; ACOO: acetoxy, and also propionoxy; ACSO: thio(no)acetoxy, and also thioL(no)propinoxy; hydroxyalkyl: hydroxymethyl, 1-hydroxyethyl or 2-hydroxyethyl; Mercaptoalkyl: mercaptomethyl, 1-mercaptoethyl or 2-mercaptoethyl; NHA: methylamino, and also ethylamino; $NA_2$: dimethylamino, and also diethylamino; ASO: methylsulfinyl, also ethylsulfinyl; $ASO_2$: methylsulfonyl, and also ethylsulfonyl; AO—SO: methoxysulfinyl, and also ethoxysulfinyl; AO—$SO_2$: methoxysulfonyl, and also ethoxysulfonyl; Ac—NH: acetamido, and also formamido, propionamido or benzamido; AO—CO—NH: methoxycarbonylamino, and also ethoxycarbonylamino; HANSO: methylaminosulfinyl, and also ethylaminosulfinyl; $A_2$NSO: dimethylaminosulfinyl, and also diethylaminosulfinyl; $HANSO_2$: methylaminosulfonyl, and also ethylaminosulfonyul; $A_2NSO_2$: dimethylaminosulfonyl, and also diethylaminosulfonyl; HANCO: N-methylcarbamoyl, and also N-ethylcarbamoyl; $A_2$NOC: N,N-dimethylcarbamoyl, and also N,N-diethylcarbamoyl; HANCS: N-methylthiocarbamoyl, and also N-ethylthiocarbamoyl; $A_2$NCS: N,N-dimethylthiocarbamoyl, and also N,N-diethylthiocarbamoyl; ASONH: methylsulfinylamino, and also ethylsulfinylamino; $ASO_2NH$: methylsulfonylamino, and also ethylsulfonylamino; AOSONH: methoxysulfinylamino, and also ethoxysulfinylamino; $AOSO_2NH$: methoxysulfonylamino, and also ethoxysulfonylamino; ACO-alkyl: 2-oxopropyl, 2-oxobutyl, 3-oxobutyl or 3-oxopentyl; nitroalkyl: nitromethyl, 1-nitroethyl or 2-nitroethyl; cyanoalkyl: cyanomethyl, 1-cyanoethyl or 2-cyanoethyl; A—C(=NOH): 1-oximinoethyl, and also 1oximinopropyl; A—C(=$NNH_2$): 1-hydrazonoethyl, and also 1-hydrazonopropyl.

The radicals $R^6$ and $R^7$ are preferably located in the 6-position and 7-position in the tetralin system. They can, however, also be located in the 5-and 6-, 5- and 7-, 5- and 8-, 6- and 8- and 7- and 8-position.

One of the radicals $R^6$ and $R^7$ is preferably H, while the other is other than H. This other radical is preferably located in the 6-position, but also in the 5-, 7- or 8-position, and is preferably CN or $NO_2$, and also preferably CHO, ACO (in particular acetyl), AOOC (in particular methoxycarbonyl or ethoxycarbonyl), ACOO (in particular acetoxy), and also preferably F, Cl, Br, I, $CF_3$, $H_2NCO$, $H_2NCS$ or $NH_2$.

The radical $R^8$ is preferably H and also preferably methyl or ethyl.

Accordingly, the invention relates in particular to compounds of the formula I in which at least one of the radicals mentioned has one of the preferred meanings indicated above. Some preferred groups of compounds can be expressed by means of the following formulae Ia to Ii, which correspond to the formula I and in which the radicals not designated in detail have the meaning indicated in formula I, but in which however: in Ia $R^1$ and $R^2$ are each A; in Ib $R^1$ and $R^2$ are each $CH_3$; in Ic $R^1$ and $R^2$ are together alkylene having 3–6 C atoms; in Id $R^5$-Z- is 2-oxo-1,2-dihydro-1-pyridyl, 2-oxo-4-hydroxy-1,2-dihydro-1-pyridyl or 3-hydroxy-6-oxo-1,6-dihydro-1-pyridazinyl; in Ie $R^5$-Z- is 2-pyridyloxy, 2-hydroxy-4-pyridyloxy or 6-hydroxy-3-pyridazinyloxy; in If $R^5$-Z- is 2-oxo-1,2-dihydro-1-pyridyl; in Ig $R^1$ and $R^2$ are each $CH_3$ or together are alkylene having 3–6 C atoms, $R^5$ is 2-oxo-1,2-dihydro-1-pyridyl, 2-oxo-4-hydroxy-1,2-dihydro-1-pyridyl or 3-hydroxy-6-oxo-1,6-dihydro-1-pyridazinyl and $R^8$ is H or $CH_3$; in Ih $R^1$ and $R^2$ are each $CH_3$, $R^5$ is 2-oxo-1,2-dihydro-1-pyridyl, 2-oxo-4-hydroxy-1,2-dihydro-1-pyridyl or 3-hydroxy-6-oxo-1,6-dihydro-1-pyridazinyl and $R^8$ is H or $CH_3$; in Ii $R^1$ and $R^2$ are each $CH_3$, $R^5$ is 2-oxo-1,2-dihydro-1-pyridyl and $R^8$ is H or $CH_3$.

Compounds of the formulae I' and also Ia' to Ii' which correspond to the formulae I and Ia to Ii, but in which additionally in each case $R^3$ is OH, OCHO or $OCOCH_3$ and $R^4$ is H, are also preferred.

Compounds of the formulae I" and also Ia" to Ii" which correspond to the formulae I and also Ia to Ii, but in which additionally in each case $R^3$ and $R^4$ together are a bond, are also preferred.

Preference also attaches to compounds of the formulae I, I', I", Ia to Ii, Ia' to Ii' and Ia" to Ii" in which additionally in each case
(a) $R^6$ is other than H and $R^7$ is H; (b) $R^6$ is other than H and is in the 6-position and $R^7$ is H; (c) $R^6$ is $NO_2$, CN, CHO, ACO, HOOC, AOOC, ACOO, F, Cl, Br, I, $CF_3$, $H_2NCO$, $H_2NCS$ or $NH_2$ and $R^7$ is H; (d) $R^6$ is $NO_2$, CN, CHO, ACO, HOOC, AOOC, ACOO, F, Cl, Br, I, $CF_3$, $H_2NCO$, $H_2NCS$ or $NH_2$ and is in the 6-position and $R^7$ is H; (e) $R^6$ is $NO_2$, CN, CHO, $CH_3CO$, $CH_3OOC$, $C_2H_5OOC$ or $CH_3COO$ and $R^7$ is H; (f) $R^6$ is $NO_2$, CN, CHO, $CH_3CO$, $CH_3OOC$, $C_2H_5OOC$ or $CH_3COO$ and is in the 6-position and $R^7$ is H; (g) $R^6$ is $NO_2$ or CN and $R^7$ is H; (h) $R^6$ is $NO_2$ or CN and is in the 6-position and $R^7$ is H; (i) $R^6$ is CN and $R^7$ is H; (j) $R^6$ is CN and is in the 6-position and $R^7$ is H.

Compounds of the formulae I, I', I", Ia to Ii, Ia' to Ii', Ia" to Ii" and of the other groups of compounds characterized above as preferred in which additionally $R^8$ is H, are particularly preferred.

Moreover, in the preceding and following text, the radicals $R^1$ to $R^8$, A, "-alkyl" and Ac have the meanings indicated in formula I, unless anything to the contrary is expressly indicated.

The invention also relates to a process for the preparation of tetralin derivatives of the formula I according to claim 1, characterized in that a tetralin of the formula II

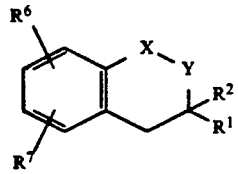

wherein X—Y is

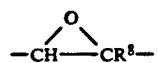

or —CHE—$CR^3R^8$— and E is Cl, Br, I or a reactive esterified OH group and $R^1$, $R^2$, $R^3$, $R^6$, $R^7$, and $R^8$ have the meanings indicated in formula I, is reacted with a compound of the formula III

R⁵—ZH      III wherein $R^5$ and Z have the meanings indicated in formula I, or is reacted with a reactive derivative thereof, and/or a compound of the formula I wherein $R^3$ is OH and $R^4$ is H is dehydrated, and/or one or more of the radicals $R^3$, $R^5$, $R^6$ and/or $R^7$ in a compound of the formula I are converted into other radicals $R^3$, $R^5$, $R^6$ and/or $R^7$, and/or a basic compound of the formula I is converted by treatment with an acid into one of the its acid addition salts.

In other respects the compounds of the formula I are prepared by methods known per se, such as are described in the literature (for example in the standard works such as Houben-Weyl, Methoden der organischen Chemie ["Methods of organic chemistry"], Georg-Thieme-Verlag, Stuttgart; Organic Reactions, John Wiley & Sons Inc., New York; and also in the paten applications indicated above), specifically under reaction conditions which are known and suitable for the reactions mention. In this respect it si also possible to make use of variants which are known per se but not mentioned here in detail.

If desired, the starting materials can also be formed in situ in a process in which they are not isolated from the reaction mixture, but are immediately reacted further to give the compounds of the formula I.

The compounds of the formula I are preferably prepared by reacting compounds of the formula II with compounds of the formula III, preferably in the presence of an inert solvent at temperatures between about 0 and 150°. In this process it is possible, irrespective of the reaction conditions and the structure of the starting materials, for compounds of the formula I wherein $R^3$ is H and $R^4$ is OH or wherein $R^3$ and $R^4$ together are a double bond to be formed alongside one another. Furthermore, if starting materials of the formula III containing a —CO—NH— group (for example 1H-2-pyridone) are used, it is possible for compounds of the formula I which are attached to the tetralin ring via the N atom [for example 4-(2-oxo-1,2-dihydropyridyl)-tetralins] or via an O bridge [for example 4-(2-pyridyloxy)-tetralins] to be formed alongside one another.

Starting materials of the formula II in which

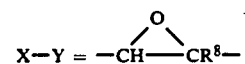

(3,4-epoxytetralins) are preferred.

As a rule, the starting materials II and III are known. Insofar as they are not known, they can be prepared by methods known per se. Thus, 7-cyano-2-bromo-3,3-dimethyl-1,2,3,4-tetrahydro-1-naphthol (II, $R^1=R^2=CH_3$, X—Y=—CHOH—CHBr—, $R^6$=6-CN and $R^7$=H) and 7-cyano-1,2-epoxy-3,3-dimethyl-1,2,3,4-tetrahydronaphthalene ("IIa"; =II, $R^1=R^2=CH_3$,

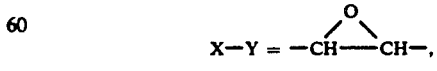

$R^6$=6-CN and $R^7$=H) are described in EP-A-168,619.

In compounds of the formula II wherein —X—Y— is —CHE—$CR^3R^8$—, suitable "reactive esterified OH groups" are especially alkylsulfonyloxy having 1–6 C atoms (for example methanesulfonyloxy) and arylsulfonyloxy having 6–10 C atoms (for example benzenesulfonyloxy, p-toluenesulfonyloxy, 1-naphthalenesulfonyloxy or 2-naphthalenesulfonyloxy).

Suitable reactive derivatives of III are the corresponding salts, for example the Na or K salts, which can also be formed in situ.

In the reaction of II with III it is preferable to carry out the reaction in the presence of a base. Examples of suitable bases are alkali metal hydroxides, carbonates, alcoholates, hydrides or amides or alkaline earth metal hydroxides, carbonates, alcoholates, hydrides or amides, such as NaOH,KOH, Ca(OH)$_2$, Na$_2$CO$_3$, K$_2$CO$_3$, Na or K methylate, ethylate or tert.-butylate, NaH, KH, CaH$_2$, NaNH$_2$ or KNH$_2$, and also organic bases such as triethylamine or pyridine, which can also be used in excess and can then at the same time serve as the solvent.

Suitable inert solvents are, in particular, alcohols, such as methanol, ethanol, isopropanol, n-butanol or tert.-butanol; ethers, such as diethyl ether, diisopropyl ether, tetrahydrofuran or dioxane; glycol ethers, such as ethylene glycol monomethyl or monoethyl ether (methylglycol or ethylglycol), ethylene glycol dimethyl ether (diglyme); ketones such as acetone or butanone; nitriles, such as acetonitrile. Nitro compounds, such as nitromethane or nitrobenzene; esters, such as ethyl acetate; amides, such as dimethylformamide (DMF), dimethylacetamide or phosphoric hexamethyltriamide; sulfoxides, such as dimethylsulfoxide (DMSO); chlorinated hydrocarbons, such as methylene dichloride, chloroform, trichoroethylene, 1,2-dichloroethane or carbon tetrachloride; or hydrocarbons, such as benzene, toluene or xylene. Mixtures of these solvents with one another are also suitable.

If the reaction is carried out with NaH in DMSO at room temperature, the preferred compounds of the formula I in which R$^3$ and R$^4$ together are a bond and Z is a bond are obtained to a very predominant extent; thus with 1H-2-pyridone, for example, the corresponding 1,2-dihydro-(2-oxo-1,2-dihydropyridyl)-naphthalenes are formed.

The epoxide II

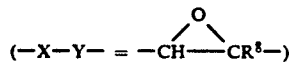

can also be prepared in situ, for example by the action of a base on the corresponding bromohydrin.

A compound of the formula I wherein R$^3$ is OH and R$^4$ is H can be converted into a compound of the formula I wherein R$^3$ and R$^4$ together are a bond by treatment with a dehydrating agent. This can be done, for example, by the action of one of the bases indicated, for example NaH, in one of the solvents indicated, for example DMSO, at temperatures between 0° and 150°.

It is also possible to convert one or more of the radicals R$^3$, R$^5$, R$^6$ and/or R$^7$ in a compound of the formula I into other radicals R$^3$, R$^5$, R$^6$ and/or R$^7$.

For example, it is possible to replace an H atom by a halogen atom by halogenation or by a nitro group by means of nitration, and/or to reduce a nitro group to an amino group and/or to alkylate or acylate an amino or hydroxyl group and/or to convert a cyano group (for example with HCl in water/methanol at 20°-100°;) into a carboxyl group or (for example using Raney nickel in water/acetic acid/pyridine in the presence of sodium phosphate) into a formyl group or (for example by means of KOH in tert.-butanol) into a carbamoyl group or (for example by means of H$_2$S in pyridine/triethylamine) into a thiocarbamoyl group, and/or to convert a —CO—NH— group into a —CS—NH— or a —C(SH)=N— group (for example by means of P$_2$S$_5$ or the Lawesson reagent in toluene).

Nitration is possible under customary conditions, for example using a mixture of concentrated HNO$_3$ and concentrated H$_2$SO$_4$ at temperatures between 0° and 30°. If at least one of the substituents R$^6$ and R$^7$ is an electro-negative group, such as CN or NO$_2$, the nitration takes place mainly on the radical R$^5$; in other cases, as a rule, mixtures in which the nitro groups can be on the radical R$^5$ or on the benzene ring are obtained.

Analogous considerations apply to halogenation, which can be carried out, for example, by means of elementary chlorine or bromine in one of the customary inert solvents at temperatures between about 0° and 30°.

A primary or secondary amino group and/or an OH group can be converted into the corresponding secondary or tertiary amino group and/or alkoxy group by treatment with alkylating agents. Examples of suitable alkylating agents are compounds of the formulae A—Cl, A—Br or A—I or corresponding esters of sulfuric acid or sulfonic acids, such as methyl chloride, bromide or iodide, dimethyl sulfate or methyl p-toluenesulfonate. It is also possible, for example, to introduce one or two methyl groups by means of formaldehyde in the presence of formic acid. The alkylation is preferably carried out in the presence or absence of one of the inert solvents mentioned, for example DMF, at temperatures between about 0° and about 120°, and a catalyst can also be present, preferably a base, such as potassium tert.-butylate or NaH.

Suitable acylating agents for acylating amino or hydroxyl groups are preferably the halides (for example chlorides or bromides) or anhydrides of carboxylic acids of the formula Ac—OH, for example acetic anhydride, propionyl chloride, isobutyryl bromide, formic-/acetic anhydride or benzoyl chloride. The addition of a base, such as pyridine or triethylamine, during the acylation is possible. Acylation is preferably carried out in the presence or absence of an inert solvent, for example a hydrocarbon, such as toluene, a nitrile, such as acetonitrile, an amide, such as DMF, or an excess of a tertiary base, such as pyridine or triethylaine, at temperatures between about 0° and about 160°, preferably between 20° and 120°. Formylation can also be carried out by means of formic acid in the presence of pyridine.

A base of the formula I can be converted into the corresponding acid addition salt by means of an acid. Acids suitable for this reaction are, in particular, those which afford physiologically acceptable salts. Thus it is possible to use inorganic acids, for example sulfuric acid, nitric acid, hydrogen halide acids, such as hydrochloric acid or hydrobromic acid, phosphoric acids, such as orthophosphoric acid, or sulfamic acid, and also organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 2-phenylpropionic or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalene monosulfonic and naphthalene disulfonic acids or laurylsulfuric acid. Salts with physiologically unacceptable acids, for example picrates, can be used to purify the compounds of the formula I.

The compounds of the formula I can possess one or more chiral centers. When prepared, therefore, they can be obtained as racemates or, if optically active starting materials are used, also in an optically active form. If the compounds have two or more chiral centers, they can then be obtained in the course of the synthesis as mixtures of racemates from which the individual racemates can be isolated in a pure form, for example by recrystallization from inert solvents. Thus, for example, compounds of the formula I wherein $R^1 = R^2$, $R^3 = OH$ and $R^4 = H$ have two chiral centers; what is formed when prepared by reacting II with III is, however, very predominantly only one racemate having the substituents $R^3 = OH$ and $R^5 - Z$ in the trans-position. Resulting racemates can, if desired, be resolved into their enantiomers mechanically or chemically by methods known per se. Thus, diastereomers can be formed from the racemate by reaction with an optically active resolving agent. Examples of suitable resolving agents for basic compounds of the formula I are optically active acids, such as the D-forms and L-forms of tartaric acid, dibenzoyl tartaric acid, diacetyl tartaric acid, camphorsulfonic acids, mandelic acid, malic acid or lactic acid. Carbinols (I, $R^3 = OH$) can also be esterified by means of chiral acylating reagents, for example D-α-methylbenzyl or L-α-methylbenzyl isocyanate, and can then be resolved (compare E)-A1-120,428). The different forms of he diastereomers can be resolved in a manner known per se, for example by fractional crystallization, and the enantiomers of the formula I can be liberated from the diastereomers in a manner known per se. Resolutions of enantiomers can also be carried out by chromatography on optically active supporting materials.

The compounds of the formula I and their physiologically acceptable salts can be used for the preparation of pharmaceutical formulations, particularly by a non-chemical route. In this regard they can be brought into a suitable dosage form together with at least one solid, liquid and/or semi-liquid excipient or auxiliary and, if appropriate, in combination with one or more further active compound(s).

The invention also relates to agents, in particular pharmaceutical formulations, containing at least one compound of the formula I and/or one of its physiologically acceptable salts.

These formulations can be used as medicaments in human or veterinary medicine. Suitable excipients are organic or inorganic substances which are suitable for enteral (for example oral) or parenteral administration or for topical application and which do not react with the new compounds, for example water, vegetable oils, benzyl alcohols, polyethylene glycols, glycerol triacetate, gelatin, carbohydrates, such as lactose or starch, magnesium stearate, talc, lanolin or petroleum jelly. Tablets, coated tablets, capsules, syrups, elixirs or drops are particularly suitable for oral administration, suppositories are particularly suitable for rectal administration, solutions, preferably oily or aqueous solutions, and also suspensions, emulsions or implants are particularly suitable for parenteral administration, and ointments, creams, pastes, lotions, gels, sprays, foams, aerosols, solutions (for example solutions in alcohols, such as ethanol or isopropanol, acetonitrile, DMF, dimethylacetamide or 1,2-propanediol or mixtures thereof with one another and/or with water) or dusting powders are particularly suitable for topical application. The new compounds can also be lyophilized, and the resulting lyophilizates can be used, for example, for the production of injection preparations. Liposomal formulations are also particularly suitable for topical application. The formulations indicated can be sterilized and/or can contain auxiliaries, such as lubricants, preservatives, stabilizers and/or wetting agents, emulsifiers, salts for influencing the osmotic pressure, buffer substances, colorants, flavorings and/or aroma substances. If desired, they can also contain one or more further active compounds, for example one or more vitamins.

The compounds of the formula I and their physiologically acceptable salts can be administered to humans or animals, in particular mammals, such as monkeys, dogs, cats, rats or mice, and can be used in the therapeutic treatment of the human or animal body and also in combating diseases, particularly in the therapy and/or prophylaxis of disorders of the cardiovascular system, especially decompensated cardiac insufficiency, angina pectoris, arrhythmia, peripheral or cerebral vascular diseases and also illnesses associated with high blood pressure, and also diseases associated with changes in the non-vascular muscular system, for example asthma or incontinence of the bladder.

In this regard the substances according to invention are administered, as a rule, analogously to known anti-angine or hypotensive agents, for example Nicorandil or Cromakalim, preferably in dosages between about 0.01 and 5 mg, in particular between 0.02 and 0.5 mg, per dosage unit. The daily dose is preferably between about 0.0001 and 0.1, in particular between 0.0003 and 0.01, mg/kg of body weight. The special dose for each particular patient depends, however, on a very wide variety of factors, for example on the activity of the particular compound employed, on the age, body weight, general state of health, sex, diet, time and route of administration, excretion rate, combination of medicaments and the severity of the particular disease for which the therapy is used. Oral administration is preferred.

Particularly in the case of topical application, the compounds of the formula I and their salts are also suitable for the treatment of alopecia, including androgenic alopecia and Alopecia areata. Pharmaceutical formulations which are suitable for the topical treatment of the scalp and which are mentioned above are especially used for this purpose. They contain about 0.005 to 10, preferably 0.5 to 3, % by weight of at least one compound of the formula I and/or at least one of its salts. In other respects these compounds can be used against alopecia analogously to the instructions in WO 88/00822.

Upon further study of the specification and appended claims, further objects and advantages of this invention will become apparent to those skilled in the art. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, cited above and below, and of corresponding application Federal Republic of Germany P 38 37 809.4, filed Nov. 8, 1988, are hereby incorporated by reference.

In the following examples "customary working up" means as follows:

If necessary, water is added, the mixture is extracted with an organic solvent, such as ethyl acetate, the phases are separated, the organic phase is dried over sodium sulfate, filtered and evaporated ad the residue is purified by chromatography and/or crystallization.

EXAMPLE 1

A solution of 9.2 g of 1H-2-pyridone in 100 ml of DMSO is added dropwise to a suspension of 3.1 g of NaH in 100 ml of anhydrous DMSO, with stirring and while $N_2$ is passed in. After stirring for 1 hour, a solution of 15 g of IIa in 125 ml of DMSO is added dropwise and the mixture is stirred at 20° C. for a further 17 hours. Saturated NaCl solution is then added, the mixture is extracted with ethyl acetate, the extract is washed with water, dried over sodium sulfate and evaporated and the residue is chromatographed on silica gel (8:2 methylene dichloride/ethyl acetate). This gives 2,2-dimethyl-4-(2-oxo-1,2-dihydro-1-pyridyl)-6-cyano-1,2-dihydronaphthalene ("A"), m.p. 112°–112.5°.

2,2-Dimethyl-4-(2-oxo-4-hydroxy-1,2-dihydro-1-pyridyl)-6-cyano-1,2-dihydronaphthalene, m.p. 222° is obtained analogously using 2,4-dihydroxypyridine (=4-hydroxy-1H-2-pyridone).

2,2-Dimethyl-4-(3-hydroxy-6-oxo-1,6-dihydro-1-pyridazinyl)-6-cyano-1,2-dihydronaphthalene is obtained analogously using 3,6-dihydroxypyridazine (=3-hydroxy-6-oxo-1,6-dihydropyridazine).

The following are obtained analogously:

2,2-dimethyl-4-(2-thioxo-1,2-dihydro-1-pyridyl)-6-cyano-1,2dihydronaphthalene
2,2-dimethyl-4-(2-oxo-3-chloro-1,2-dihydro-1-pyridyl)-6-cyano-1,2-dihydronaphthalene
2,2-dimethyl-4-(2-oxo-5-chloro-1,2-dihydro-1-pyridyl)-6-cyano-1,2-dihydronaphthalene
2,2-dimethyl-4-(2-oxo-6-chloro-1,2-dihydro-1-pyridyl)-6-cyano-1,2-dihydronaphthalene
2,2-dimethyl-4-(2-oxo-3-hydroxy-1,2-dihydro-1-pyridyl)-6-cyano-1,2-dihydronaphthalene
2,2-dimethyl-4-(2-oxo-5-hydroxy-1,2-dihydro-1-pyridyl)-6-cyano-1,2-dihydronaphthalene
2,2-dimethyl-4-(2-oxo-3-methoxy-1,2-dihydro-1-pyridyl)-6-cyano-1,2-dihydronaphthalene
2,2-dimethyl-4-(2-oxo-3-acetoxy-1,2-dihydro-1-pyridyl)-6-cyano-1,2-dihydronaphthalene
2,2-dimethyl-4-(2-oxo-3-nitro-1,2-dihydro-1-pyridyl)-6-cyano-1,2-dihydronaphthalene
2,2-dimethyl-4-(2-oxo-5-nitro-1,2-dihydro-1-pyridyl)-6-cyano-1,2-dihydronaphthalene
2,2-dimethyl-4-(2-oxo-3-amino-1,2-dihydro-1-pyridyl)-6-cyano-1,2-dihydronaphthalene
2,2-dimethyl-4-(2-oxo-5-amino-1,2-dihydro-1-pyridyl)-6-cyano-1,2-dihydronaphthalene
2,2-dimethyl-4-(2-oxo-3-acetamido-1,2-dihydro-1-pyridyl)-6-cyano-1,2-dihydronaphthalene
2,2-dimethyl-4-(2-oxo-5-acetamido-1,2-dihydro-1-pyridyl)-6-cyano-1,2-dihydronaphthalene
2,2-dimethyl-4-(2-oxo-3-carboxy-1,2-dihydro-1-pyridyl)-6-cyano-1,2-dihydronaphthalene
2,2-dimethyl-4-(2-oxo-3,5-dichloro-1,2-dihydro-1-pyridyl)-6-cyano-1,2-dihydronaphthalene
2,2-dimethyl-4-(2-oxo-3,5-dibromo-1,2-dihydro-1-pyridyl)-6-cyano-1,2-dihydronaphthalene
2,2-dimethyl-4-(2-oxo-3-chloro-5-nitro-1,2-dihydro-1-pyridyl)-6-cyano-1,2-dihydronaphthalene
2,2-dimethyl-4-(2-oxo-3-nitro-5-chloro-1,2-dihydro-1-pyridyl)-6-cyano-1,2-dihydronaphthalene
2,2-dimethyl-4-(2-oxo-3-bromo-5-nitro-1,2-dihydro-1-pyridyl)-6-cyano-1,2-dihydronaphthalene
2,2-dimethyl-4-(2-oxo-3-nitro-5-bromo-1,2-dihydro-1-pyridyl)-6-cyano-1,2-dihydronaphthalene
2,2-dimethyl-4-(2-oxo-3,5-dinitro-1,2-dihydro-1-pyridyl)-6-cyano-1,2-dihydronaphthalene
2,2-dimethyl-4-(2-oxo-3-chloro-5-amino-1,2-dihydro-1-pyridyl)-6-cyano-1,2-dihydronaphthalene
2,2-dimethyl-4-(2-oxo-3-amino-5-chloro-1,2-dihydro-1-pyridyl)-6-cyano-1,2-dihydronaphthalene
2,2-dimethyl-4-(2-oxo-3-bromo-5-amino-1,2-dihydro-1-pyridyl)-6-cyano-1,2-dihydronaphthalene
2,2-dimethyl-4-(2-oxo-3-amino-5-bromo-1,2-dihydro-1-pyridyl)-6-cyano-1,2-dihydronaphthalene
2,2-dimethyl-4-(2-oxo-3-chloro-5-acetamido-1,2-dihydro-1-pyridyl)-6-cyano-1,2-dihydronaphthalene
2,2-dimethyl-4-(2-oxo-3-acetamido-5-chloro-1,2-dihydro-1-pyridyl)-6-cyano-1,2-dihydronaphthalene
2,2-dimethyl-4-(2-oxo-3-bromo-5-acetamido-1,2-dihydro-1-pyridyl)-6-cyano-1,2-dihydronaphthalene
2,2-dimethyl-4-(2-oxo-3-acetamido-5-bromo-1,2-dihydro-1-pyridyl)-6-cyano-1,2-dihydronaphthalene
2,2-dimethyl-4-(2-oxo-1,2-dihydro-1-pyridyl)-6-acetyl-1,2-dihydronaphthalene
2,2-dimethyl-4-(2-oxo-1,2-dihydro-1-pyridyl)-6-methoxycarbonyl-1,2-dihydronaphthalene
2,2-dimethyl-4-(2-oxo-1,2-dihydro-1-pyridyl)-6-ethoxycarbonyl-1,2-dihydronaphthalene
2,2-dimethyl-4-(2-oxo-1,2-dihydro-1-pyridyl)-6-fluoro-1,2-dihydronaphthalene
2,2-dimethyl-4-(2-oxo-1,2-dihydro-1-pyridyl)-6-chloro-1,2-dihydronaphthalene
2,2-dimethyl-4-(2-oxo-1,2-dihydro-1-pyridyl)-6-bromo-1,2-dihydronaphthalene
2,2-dimethyl-4-(2-oxo-1,2-dihydro-1-pyridyl)-6-nitro-1,2-dihydronaphthalene
2,2-dimethyl-4-(2-oxo-1,2-dihydro-1-pyridyl)-6-trifluoromethyl-1,2-dihydronaphthalene
2,2-dimethyl-4-(2-oxo-1,2-dihydro-1-pyridyl)-6-acetamido-1,2-dihydronaphthalene
2,2-dimethyl-4-(2-oxo-1,2-dihydro-1-pyridyl)-7-cyano-1,2-dihydronaphthalene
2,2-dimethyl-4-(2-oxo-1,2-dihydro-1-pyridyl)-6-acetamido-7-nitro-1,2-dihydronaphthalene
2-4-(2-oxo-1,2-dihydro-1-pyridyl)-6-cyano-1,2-dihydronaphthalene
2-methyl-2-ethyl-4-(2-oxo-1,2-dihydro-1-pyridyl)-6-cyano-1,2-dihydronaphthalene
2,2-diethyl-4-(2-oxo-1,2-dihydro-1-pyridyl)-6-cyano-1,2-dihydronaphthalene
2,2-tetramethylene-4-(2-oxo-1,2-dihydro-1-pyridyl)-6-cyano-1,2-dihydronaphthalene
2,2-pentamethylene-4-(2-oxo-1,2-dihydro-1-pyridyl)-6-cyano-1,2-dihydronaphthalene
2,2,3-trimethyl-4-(2-oxo-1,2-dihydro-1-pyridyl)-6-cyano-1,2-dihydronaphthalene
2,2-dimethyl-4-(6-oxo-1,6-dihydro-1-pyridazinyl)-6-cyano-1,2-dihydronaphthalene
2,2-dimethyl-4-(3-ethoxycarbonyl-6-oxo-1,6-dihydro-1-pyridazinyl)-6-cyano-1,2-dihydronaphthalene
2,2-dimethyl-4-(2-oxo-1,2-dihydro-1-pyrimidinyl)-6-cyano-1,2-dihydronaphthalene 2,2-dimethyl-4-(2-oxo-4-hydroxy-1,2-dihydro-1-
  pyrimidinyl)-6-cyano-1,2-dihydronaphthalene
2,2-dimethyl-4-(6-oxo-1,6-dihydro-1-pyrimidinyl)-6-
  cyano-1,2-dihydronaphthalene
2,2-dimethyl-4-(4-hydroxy-6-oxo-1,6-dihydro-1-
  pyrimidinyl)-6-cyano-1,2-dihydronaphthalene
2,2-dimethyl-4-(2-oxo-1,2-dihydro-1-pyrazinyl)-6-
  cyano-1,2-dihydronaphthalene
2,2-dimethyl-4-(2-oxo-2,5-dihydro-1-pyrrolyl)-6-cyano-
  1,2-dihydronaphthalene
2,2dimethyl-4-(2-oxo-4-hydroxy-1,2-dihydro-1-
  pyridyo)-6-bromo-1,2-dihydronaphthalene
2,2-dimethyl-4-(2-oxo-4-hydroxy-1,2-dihydro-1-
  pyridyl)-6-nitro-1,2-dihydronaphthalene
2,2-dimethyl-4-(2-oxo-4-hydroxy-1,2-dihydro-1-
  pyridyl)-6-methoxycarbonyl-1,2-dihydronaphthalene
2,2-dimethyl-4-(3-hydroxy-6-oxo-1,6-dihydro-1-
  pyridazinyl)-6-bromo-1,2-dihydronaphthalene
2,2-dimethyl-4-(3-hydroxy-6-oxo-1,6-dihydro-1-
  pyridazinly)-6-nitro-1,2-dihydronaphthalene
2,2-dimethyl-4-(3-hydroxy-6-oxo-1,6-dihydro-1-
  pyridazinyl)-6-methoxycarbonyl-1,2-dihydronaph-
  thalene.

EXAMPLE 2

19.9 g of IIa, 9.5 g of 1H-2-pyridone, 5 ml of pyridine and 50 ml of ethanol is heated at 100° (in a tube) for 2 hours. The mixture is evaporated and worked up in the customary manner to give, after separation by chromatography, "A" (m.p. 112°–112.5°) as well as 2,2-dimethyl-4-(2-oxo-1,2-dihydro-1-pyridyl)-6-cyano-1,2,3,4-tetrahydro-3-naphthol ("B"; m.p. 201°–203°) and 2,2-dimethyl-4-(2-pyridyloxy)-6-cyano-1,2,3,4-tetrahydro-3-naphthol (m.p. 113°–114°.

The compounds indicated in Example 1 and also the corresponding 3,4-dihydro-3-hydroxy compounds are obtained analogously, for example:
2,2-dimethyl-4-(2-oxo-4-hydroxy-1,2-dihydro-1-
  pyridyl)-6-cyano-1,2,3,4-tetrahydro-3-naphthol
2,2-dimethyl-4-(3-hydroxy-6-oxo-1,6-dihydro-1-
  pyridazinyl)-6-cyano-1,2,3,4-tetrahydro-3-naphthol
2,2-dimethyl-4-(2-oxo-1,2-dihydro-1-pyridyl)-6-nitro-
  1,2,3,4-tetrahydro-3-naphthol
and also corresponding compounds in which Z=O, for example:
2,2-dimethyl-4-(2-oxo-1,2-dihydro-4-pyridyloxy)-6-
  cyano-1,2,3,4-tetrahydro-3-naphthol, m.p. 265°–269°
2,2-dimethyl-4-(6-oxo-1,6-dihydro-3-pyridazinyloxy)-6-
  cyano-1,2,3,4-tetrahydro-3-naphthol
2,2-dimethyl-4-(2-oxo-1,2-dihydro-4-pyridyloxy)-6-
  nitro-1,2,3,4-tetrahydro-3-naphthol.

EXAMPLE 3

1.2 g of 80% NaH is added to a solution of 3.18 g of 2,2-dimethyl-4,6-dibromo-1,2,3,4-tetrahydronaphthalene (obtainable from 2,2-dimethyl-6-bromo-1,2,3,4-tetrahydro-4-naphthol and SOBr$_2$) and 0.95 g of 2H-1-pyridone in 20 ml of DMSO, and the mixture is stirred for 3 days at 20°. Working up in the customary manner gives 2,2-dimethyl-4-(2-oxo-1,2-dihydro-1-pyridyl)-6-bromo-1,2,3,4-tetrahydronaphthalene.

EXAMPLE 4

2,2-Dimethyl-4-(3-hydroxy-2-pyridylamino)-6-cyano-1,2,3,4-tetrahydro-3-naphthol is obtained analogously to Example 2 from IIa and 2-amino-3-hydroxypyridine.

EXAMPLE 5

2,2-Dimethyl-4-(2-pyridylthio)-6-cyano-1,2,3,4-tetrahydro-3-naphthol is obtained analogously to Example 2 from IIa and 2-mercaptopyridine.

EXAMPLE 6

2,2-Dimethyl-4-(2-pyridylthio)-6-cyano-1,2-dihydronaphthalene is obtained analogously to Example 1 from IIa and 2-mercaptopyridine.

EXAMPLE 7

A mixture of 1 g of 2,2-dimethyl-4-(2-pyridylthio)-6-cyano-1,2,3,4-tetrahydro-3-naphthol, 0.3 g of NaOH and 35 ml of dioxane is boiled for 20 minutes. The mixture is cooled and filtered and the filtrate is evaporated and worked up in the customary manner to give 2,2-dimethyl-4-(2-pyridylthio)-6-cyano-1,2-dihydronaphthalene.

EXAMPLE 8

A mixture of 2 g of "B", 11.7 ml of formic acid and 3.3 ml of acetic anhydride is allowed to stand for 16 hours at 20° and is then heated at 40° for 2 hours. Evaporation and working up in the customary manner gives 2,2-dimethyl-3-formyloxy-4-(2-oxo-1,2-dihydro-1-pyridyl)-6-cyano-1,2,3,4-tetrahydronaphthalene.

EXAMPLE 9

A mixture of 1 g of "B" and 5 ml of acetic anhydride is boiled for 1 hour. The mixture is cooled and worked up in the customary manner to give 2,2-dimethyl-3-acetoxy-4-(2-oxo-1,2-dihydro-1-pyridyl)-6-cyano-1,2,3,4-tetrahydronaphthalene.

EXAMPLE 10

A solution of 1 g of 2,2-dimethyl-4-(2-oxo-1,2-dihydro-1-pyridyl)-6-nitro-1,2,3,4-tetrahydro-3-naphthol in 24 ml of methanol is hydrogenated at 20° and 1 bar over 0.5 g of 5% Pd-on-C until hydrogenation ceases. The mixture is filtered and evaporated and worked up in the customary manner (using dilute sodium hydroxide/methylene dichloride) to give 2,2-dimethyl-4-(2-oxo-1,2-dihydro-1-pyridyl)-6-amino-1,2,3,4-tetrahydro-3-naphthol.

EXAMPLE 11

A solution of 1 g of 2,2-dimethyl-4-(2-oxo-1,2-dihydro-1-pyridyl)-6-amino-1,2,3,4-tetrahydro-3-naphthol in 15 ml of formic acid and 1 ml of pyridine is boiled for 16 hours and evaporated. Working up in the customary manner gives 2,2-dimethyl-4-(2-oxo-1,2-dihydro-1-pyridyl)-6-formamido-1,2,3,4-tetrahydro-3-naphthol.

EXAMPLE 12

A mixture of 1 g of 2,2-dimethyl-4-(2-oxo-1,2-dihydro-1-pyridyl)-6-amino-1,2,3,4-tetrahydro-3-naphthol, 10 ml of acetic anhydride and 10 ml of pyridine is allowed to stand for 16 hours at 20°. Evaporation and purification by chromatography give 2,2-dimethyl-4-(2-oxo-1,2-dihydro-1-pyridyl)-6-acetamido-1,2,3,4-tretrahydro-3-naphthol.

EXAMPLE 13

HCl is passed with stirring into a boiling solution of 1 g of "A" in 50 ml of methanol and 2 ml of water for 14 hours. The mixture is cooled to 0° overnight. The precipitated 2,2-dimethyl-4-(2-oxo-1,2-dihydro-1-pyridyl)-1,2-dihydronaphthalene-6-carboxylic acid is filtered off.

EXAMPLE 14

A mixture of 2.76 g of "A", 31 g of $Na_3PO_4 \cdot 12\,H_2O$, 28 ml of pyridine, 28 ml of water, 67 ml of acetic acid and 25 g of Raney nickel (water-moist) is stirred for 3 hours at 20°. The mixture is filtered and the filtrate is worked up in the customary manner to give 2,2-dimethyl-4-(2-oxo-1,2-dihydro-1-pyridyl)-6-formyl-1,2-dihydronaphthalene.

EXAMPLE 15

2.76 g of "A" are dissolved in 40 ml of tert.-butanol, and 5.6 g of powdered KOH are added with stirring. Boiling for one hour and working up in the customary manner give 2,2-diemthyl-4-(2-oxo-1,2-dihydro-1-pyridyl)- 6-carbamoyl-1,2-dihydronaphthalene.

EXAMPLE 16

$H_2S$ is passed, at 20°, into a solution of 2.76 g of ¢A" in a mixture of 20 ml of pyridine and 10 ml of triethylamine for 5 hours, the mixture is evaporated and working up in the customary manner gives 2,2-dimethyl-4-(2-oxo-1,2-dihydro-1-pyridyl)-6-thiocarbamoyl-1,2-dihydronaphthalene.

EXAMPLE 17

A mixture of 2.76 g of "A", 8.08 g of Lawesson reagent and 50 ml of toluene is boiled under $N_2$ for 1 hour. Working up in the customary manner gives 2,2-dimethyl-4-(2-thioxo-1,2-dihydro-1-pyridyl)-6-cyano-1,2-dihydronaphthalene.

The following are obtained analogously:
2,2-dimethyl-4-(2-thioxo-1,2-dihydro-1-pyridyl)-6-bromo-1,2-dihydronaphthalene
2,2-dimethyl-4-(2-thioxo-1,2-dihydro-1-pyridyl)-6-nitro-1,2-dihydronaphthalene.

EXAMPLE 18

A mixture of 310 mg of 2,2-dimethyl-4-(2-oxo-1,2-dihydro-4-pyridyloxy)-6-cyano-1,2,3,4-tetrahydro-3-naphthol, 20 ml of acetone, 400 mg of $K_2CO_3$ and 0.2 ml of dimethylsulfate is boiled for 2 hours. The mixture is filtered and the filtrate is worked up in the customary manner to give 2,2-dimethyl-4-(1-methyl-2-oxo-1,2-dihydro-4-pyridyloxy)-6-cyano-1,2,3,4-tetrahydro-3-naphthol.

EXAMPLE 19

A mixture of 311 mg of 2,2-dimethyl-4-(6-oxo-1,6-dihydro-3-pyridazinyloxy)-6-cyano-1,2,3,4-tetrahydro-3-naphthol, 1 g of $K_2CO_3$, 0.65 ml of dimethyl sulfate and 16 ml of DMF is boiled for 3 hours and worked up in the customary manner. This gives 2,2-dimethyl-4-(6-methoxy-3-pyridazinyloxy)-6-cyano-1,2,3,4-tetrahydro-3-naphthol.

EXAMPLE 20

Analogously to Example 2 1-(2-oxo-1,2-dihydro-1-pyridyl)-1,2,3,4-tetrahydro-2-naphthol, m.p. 180°-181° is obtained from 1,2-epoxy-1,2,3,4-tetrahydronaphthalene and 1H-2-pyridone. In addition, 1-(2-oxo-1,2-dihydro-1-pyridyl)-3,4-dihydronaphthalene is formed.

Analogously, 1-(2-oxo-1,2-dihydro-1-pyridyl)-3,3-dimethyl-1,2,3,4-tetrahydro-2-naphthol and 1-(2-oxo-1,2-dihydro-1-pyridyl)-3,3-dimethyl-3,4-dihydronaphthalene are obtained with 1,2-epoxy-3,3-dimethyl-1,2,3,4-tetrahydronaphthalene.

Analogously, 1-(2-oxo-1,2-dihydro-1-pyridyl)-7-bromo-1,2,3,4-tetrahydro-2-naphthol and 2-(2-oxo-1,2-dihydro-1-pyridyl)-7-bromo-3,4-dihydronaphthalene are obtained with 1,2-epoxy-7-bromo-1,2,3,4-tetrahydronaphthalene.

Analogously, 1-(2-oxo-1,2-dihydro-1-pyridyl)-7-cyano-1,2,3,4-tetrahydro-2-naphthol and 1-(2-oxo-1,2-dihydro-1-pyridyl)-7-cyano-3,4-dihydronaphthalene are obtained with 1,2-epoxy-7-cyano-1,2,3,4-tetrahydronaphthalene.

Analogously, 2,2-dimethyl-4-(2-oxo-1,2-dihydro-1-pyridyl)-6-bromo-1,2,3,4-tetrahydro-3-naphthol and 2,2-dimethyl-4-(2-oxo-1,2-dihydro-1-pyridyl)-6-bromo-1,2-dihydronaphthalene are obtained with 3,4-epoxy-6-bromo-2,2-dimethyl-1,2,3,4-tetrahydronaphthalene.

Analogously, 2,2,3-trimethyl-4-(2-oxo-1,2-dihydro-1-pyridyl)-6-bromo-1,2,3,4-tetrahydro-3-naphthol and 2,2,3-trimethyl-4-(2-oxo-1,2-dihydro-1-pyridyl)-6-bromo-1,2-dihydronaphthalene are obtained with 3,4-epoxy-6-bromo-2,2,3-trimethyl-1,2,3,4-tetrahydronaphthalene.

Analogously, 2,2,3-trimethyl-4-(2-oxo-1,2,-dihydro-1-pyridyl)-6-cyano-1,2,3,4-tetrahydro-3-naphthol and 2,2,3-trimethyl-4-(2-oxo-1,2-dihydro-1-pyridyl)-6-cyano-1,2-dihydronaphthalene are obtained with 3,4-epoxy-6-cyano-2,2,3-trimethyl-1,2,3,4-tetrahydronaphthalene.

EXAMPLE 21

Analogously to Example 2, 2,2-dimethyl-4-(6-oxo-1,6-dihydro-3-pyridazinyl-thio)-6-cyano-1,2,3,4-tetrahydro-3-naphthol, m.p. 223°-225°, is obtained from IIa and 3-marcapto-6-hydroxy-pyridazine.

EXAMPLE 22

A solution of diazomethane in ether is added dropwise at 20° to a solution of 1 g of 2,2-dimethyl-4-(6-oxo-1,6-dihydro-3-pyridazinyl-thio)-6-cyano-1,2,3,4-tetrahydro-3-haphthol in 10 ml of methanol until the yellow color persists. The solution is concentrated and 2,2-dimethyl-4-(6-oxo-1-methyl-1,6-dihydro-3-pyridazinyl-thio)-6-cyano-1,2,3,4-tetrahydro-3-naphthol, m.p. 149°-151°, is obtained.

The examples below relate to pharmaceutical formulations containing compounds of the formula I or physiologically acceptable salts thereof:

EXAMPLE A

Tablets

A mixture of 1 kg of "A", 80 kg of lactose, 2 4kg of potato starch, 4 kg of talc and 2 kg of magnesium stearate is compressed in a customary manner to give tablets in such a way that each tablet contains 1 mg of active compound.

EXAMPLE B

Coated tablets

Tablets are obtained by compression analogously to Example A and are then coated in a customary manner with a coating composed of sucrose, potato starch, talc, tragacanth and a colorant.

EXAMPLE C

Capsules 1 kg of 2,2-dimethyl-4-(2-oxo-4-hydroxy-1,2-dihydro-1-pyridyl)-6-cyano-1,2-dihydronaphthalene is filled in a customary manner into hard gelatin capsules in such a way that each capsule contains 0.5 mg of active compound.

EXAMPLE D

Ampoules

A solution of 50 g of "A" in 70 l of 1,2-propanediol is made up to 100 l with twice-distilled water, and the solution is filtered under sterile conditions and poured into ampoules, which are sealed under sterile conditions. Each ampoule contains 0.5 mg of active compound.

Tablets, coated tablets, capsules or ampoules containing one or more of the remaining active compounds of the formula I and/or physiologically acceptable salts thereof can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A tetralin compound of the formula

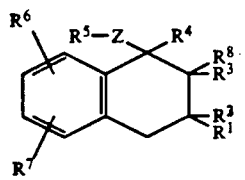

wherein
$R^1$, $R^2$ and $R^8$ are each independently H or A;
$R^3$ is H or OH;
$R^4$ is H;
$R^3$ and $R^4$ together can also be a bond;
$R^5$ is a pyridyl, pyridazinyl, oxodihydropyridyl or oxodihydropyridazinyl radical which is unsubstituted or is monosubstituted by A, OH, or OA;
$R^6$ is CN;
$R^7$ is H;
Z is O, S or a bond;
A is alkyl having 1-6 C atoms;
and physiologically acceptable salts thereof.

2. 
a) 2,2-Dimethyl-4-(2-oxo-1,2-dihydro-1-pyridyl)-6-cyano-1,2-dihydronaphthalene;
b) 2,2-dimethyl-4-(2-oxo-4-hydroxy-1,2-dihydro-1-pyridyl)-6-cyano-1,2-dihydronaphthalene; or
c) 2,2-dimethyl-4-(3-hydroxy-6-oxo-1,2-dihydro-1-pyridazinyl)-6-cyano-1,2-dihydronaphthalene,
each a compound of claim 1.

3. A compound according to claim 1, wherein $R^1$ and $R^2$ are each A.

4. A compound according to claim 1, wherein $R^1$ and $R^2$ are each $CH_3$.

5. A compound according to claim 1., wherein $R^5$-Z- is 2-oxo-1,2-dihydro-1-pyridyl, 2-oxo-4-hydroxy-1,2-dihydro-1-pyridyl or 3-hydroxy-6-oxo-1,6-dihydro-1-pyridazinyl.

6. A compound according to claim 1, wherein $R^5$-Z- is 2-pyridyloxy, 2-hydroxy-4-pyridyloxy or 6-hydroxy-3-pyridazinyloxy.

7. A compound according to claim 1, wherein $R^5$-Z- is 2-oxo-1,2-dihydro-1-pyridyl.

8. A compound according to claim 1, wherein
$R^1$ and $R^2$ are each $CH_3$;
$R^5$ is 2-oxo-1,2-dihydro-1-pyridyl, 2-oxo-4-hydroxy-1,2-dihydro-1-pyridyl or 3-hydroxy-6-oxo-1,6-dihydro-1-pyridazinyl; and
$R^8$ is H or $CH_3$.

9. A compound according to claim 1, wherein
$R^1$ and $R^2$ are each $CH_3$;
$R^5$ is 2-oxo-1,2-dihydro-1-pyridyl; and
$R^8$ is H or $CH_3$.

10. A compound according to claim 1, wherein $R^3$ and $R^4$ together are a bond.

11. A pharmaceutical composition comprising an effective amount of a compound according to claim 1 and a physiologically acceptable carrier.

12. A pharmaceutical composition according to claim 16, wherein said compound is present in an amount of about 0.1-5 mg.

13. A method of inducing a hypotensive effect comprising administering a hypotensive effective amount of a compound according to claim 1 to a patient in need thereof.

14. A method according to claim 13, wherein said compound is administered in a daily dosage of 0.001-0.1 mg/kg of body weight.

* * * * *